US011654002B2

(12) United States Patent
Hanssen (10) Patent No.: US 11,654,002 B2
(45) Date of Patent: May 23, 2023

(54) METHOD FOR DETERMINING AND VISUALIZING TOOTH MOVEMENTS AND PLANNED INSTANCES OF TOOTH REPOSITIONING (71) Applicant: SICAT GMBH & CO. KG, Bonn (DE)

(72) Inventor: Nils Hanssen, Bonn (DE)

(73) Assignee: SICAT GMBH & CO. KG, Bonn (DE)

(*) Notice: Subject to any disclaimer, the term of this patent is extended or adjusted under 35 U.S.C. 154(b) by 472 days.

(21) Appl. No.: 16/646,575

(22) PCT Filed: Sep. 7, 2018

(86) PCT No.: PCT/EP2018/074142
§ 371 (c)(1),
(2) Date: Mar. 12, 2020

(87) PCT Pub. No.: WO2019/052915
PCT Pub. Date: Mar. 21, 2019

(65) Prior Publication Data
US 2020/0268485 A1 Aug. 27, 2020

(30) Foreign Application Priority Data
Sep. 15, 2017 (DE) .................. 10 2017 121 451.8

(51) Int. Cl.
A61C 9/00 (2006.01)
G16H 50/50 (2018.01)
(Continued)

(52) U.S. Cl.
CPC ............ *A61C 9/0053* (2013.01); *A61C 7/002* (2013.01); *G16H 30/40* (2018.01); *G16H 50/50* (2018.01); *A61C 7/08* (2013.01)

(58) Field of Classification Search
CPC ......... A61C 9/0053; A61C 7/002; A61C 7/08; G16H 50/50; G16H 30/40
(Continued)

(56) References Cited

U.S. PATENT DOCUMENTS 7,013,191 B2 * 3/2006 Rubbert ................... A61C 7/12
700/118
7,134,874 B2 * 11/2006 Chishti .................... A61C 7/00
(Continued)

FOREIGN PATENT DOCUMENTS

DE 10 2007 001 684 A1 8/2008

*Primary Examiner* — Nicholas D Lucchesi
(74) *Attorney, Agent, or Firm* — Norman B. Thot (57) ABSTRACT A method for representing a change in a tooth position includes creating a volume data record of an initial position of teeth in a maxilla or mandible and ascertaining teeth boundaries therefrom. A surface data record is created following a real or virtual change in the tooth position. The surface data record includes surface data of the teeth and/or parts of the volume data record of the jaw in an altered tooth position. The surface data record is referenced with the volume data record via a reference structure. The change in the tooth position in the volume data record is transformed to align teeth boundaries with the surface data of corresponding teeth from the surface data record to move tooth structures contained in the volume data record and concealed under a surface. An altered volume record with the change in the tooth position is then outputted for representation purposes.

12 Claims, 3 Drawing Sheets (51) Int. Cl.
*G16H 30/40* (2018.01)
*A61C 7/00* (2006.01)
*A61C 7/08* (2006.01)

(58) Field of Classification Search
USPC .................................................. 433/213, 214
See application file for complete search history.

(56) References Cited

U.S. PATENT DOCUMENTS

| | | | |
|---|---|---|---|
| 7,296,996 B2* | 11/2007 | Sachdeva ............... | A61C 7/146 433/24 |
| 9,629,698 B2* | 4/2017 | Lior ........................ | A61C 11/00 |
| 9,888,983 B2* | 2/2018 | Sachdeva ............. | A61C 19/045 |
| 10,438,363 B2* | 10/2019 | Kim ....................... | A61B 5/055 |
| 10,639,135 B2* | 5/2020 | Adams .................. | A61C 19/045 |
| 2002/0025503 A1* | 2/2002 | Chapoulaud ............ | A61C 7/146 700/98 |
| 2004/0197727 A1* | 10/2004 | Sachdeva ................. | A61C 7/00 433/24 |
| 2006/0073436 A1* | 4/2006 | Raby ........................ | A61C 7/00 433/24 |
| 2006/0131770 A1* | 6/2006 | Dierkes .............. | A61C 13/0003 264/16 |
| 2009/0068617 A1* | 3/2009 | Lauren ..................... | A61C 5/77 433/213 |
| 2010/0124367 A1 | 5/2010 | Cizek | |
| 2012/0015316 A1 | 1/2012 | Sachdeva et al. | |
| 2014/0379356 A1 | 12/2014 | Sachdeva et al. | |

\* cited by examiner

METHOD FOR DETERMINING AND VISUALIZING TOOTH MOVEMENTS AND PLANNED INSTANCES OF TOOTH REPOSITIONING

CROSS REFERENCE TO PRIOR APPLICATIONS

This application is a U.S. National Phase application under 35 U.S.C. § 371 of International Application No. PCT/EP2018/074142, filed on Sep. 7, 2018 and which claims benefit to German Patent Application No. 10 2017 121 451.8, filed on Sep. 15, 2017. The International Application was published in German on Mar. 21, 2019 as WO 2019/052915 A1 under PCT Article 21(2).

FIELD

The present invention relates to methods for representing a change in a tooth position in a jaw, wherein a first volume data record comprising an initial position of a plurality of teeth in the maxilla or mandible is created within the scope of the procedure.

BACKGROUND

It is well known that orthodontic treatments, which are associated with repositioning of teeth, are currently planned and carried out on the basis of visible tooth portions. Conventional plaster models, in particular the so-called orthodontic setup, are thereby used for planning and for subsequent checkups, wherein a plaster impression of the existing situation is created during the planning, and individual teeth or tooth groups are then sawed out of the impression and reassembled in the new "ideal" position using wax. A treatment can be simulated to a certain extent using such an orthodontic setup.

In addition to this conventional type of planning on the basis of plaster models, digital surface data is sometimes also recorded using optical scanners so as to be able to include the data in the planning of a target position to be obtained by therapy. This is described, for example, in US 2012/0015316 A1. Procedures for registering images are also described in DE 10 2007 001 684 A1.

However, none of the planning methods in the field of orthodontics known to date considers the effects of the planned repositioning on the roots and on the jaw joints. Known methods thus lack any type of reference to bony anatomy concealed in the jaw. Since anatomical conditions may greatly influence the possibilities of a planned orthodontic repositioning method, taking this into account is of great interest to the treating physician.

SUMMARY

An aspect of the present invention to provide a method that can be implemented easily and cost-effectively and via which the individual anatomical conditions of a patient can be conveniently taken into account when planning an orthodontic repositioning measure. A further aspect of the present invention is to provide a corresponding system for performing the method.

In an embodiment, the present invention provides a method for representing a change in a tooth position in a jaw. The method includes creating a volume data record of an initial position of a plurality of teeth in a maxilla or in a mandible. Teeth boundaries are ascertained from the volume data record. A surface data record is created following a real change or a virtual change in the tooth position. The surface data record comprises at least one of surface data of the teeth and at least parts of the volume data record comprising the jaw in an altered tooth position. The surface data record is referenced with the volume data record via a reference structure existing in the surface data record. The reference structure is not affected by the change in the tooth position. After the referencing of the surface data record, the change in the tooth position in the volume data record is transformed via a first calculation to align the teeth boundaries ascertained from the volume data record with the surface data of corresponding teeth from the surface data record so that tooth structures contained in the volume data record and concealed under a surface are moved via the first calculation. An altered volume record is outputted for representation purposes. The altered volume record comprises the change in the tooth position ascertained by the first calculation.

BRIEF DESCRIPTION OF THE DRAWINGS

The present invention is described in greater detail below on the basis of embodiments and of the drawings in which.

DETAILED DESCRIPTION

The present invention can be summarized as follows: an optical surface data record is created following a real change in the tooth position of the patient or following a (quasi-virtual or modeled) change in the tooth position of a model, the latter change being undertaken within the planning, and a created volume data record of the patient is modeled by calculation to form an altered volume data record in accordance with these surface data that characterize the repositioning. To this end, the surface data record describing the altered situation is aligned with the tomographic data, and consequently registered. The individual teeth can be isolated in the optical surface data and can be individually aligned during this procedure. The relative transformations of the teeth become apparent by way of the different transformations of the individual tooth portions onto the tomographic data. The transformation of each individual tooth can then be applied to the tooth, and its root, visible in the tomogram.

The present invention makes possible different scenarios for creating the surface data record. The surface data record can thus be produced using an optical scanning method, with either the actually altered tooth position in the mouth of the patient, or else the modeled change on a surface model being recorded. The surface data record of the altered tooth position can, however, also be produced (virtually) by calculation on the computer by way of a simulation from an available surface data record of the original, yet to be altered tooth position.

On the basis of the modified volume data record created according to the present invention, it is then possible to see the anatomical effect of the planned repositioning or of the repositioning that has already occurred to date. This modified volume data record created by a calculated simulation makes it possible to make changes during planning or during the therapy, whereby a single volume data record, recorded in the original position of the teeth, suffices.

The procedure according to the present invention is expressed by virtue of a surface data record being created by an optical scanning method, either from a real implemented change in the tooth position in the teeth of a patient or from a virtual or modeled change in the tooth position in a surface model, wherein the surface data record contains surface data of teeth and/or of parts of the fixed jaw in the case of an altered tooth position. The volume data record, which may also be recorded at a later time in the case where the repositioning is simulated on the model, likewise comprises these parts of the fixed jaw. The surface data of the fixed part of the jaw serve as a reference structure, via which the two different data records are registered to one another. The surface data record is accordingly referenced with the volume data record, from which this reference structure is "prepared" by calculation, via the reference structure that is not affected by the change and is visible in the surface data record.

Once the surface data record has been referenced with the volume data record, the change in the tooth position is transformed into the volume data record by calculation, by virtue of boundaries of the teeth ascertained from the volume data record being aligned with surface data of the corresponding teeth from the surface data record. Together with this "aligning" of the tooth surfaces visible in the volume data record with the corresponding tooth surfaces from the surface data record, the tooth structures, such as the roots and the tooth neck situated in the gingiva, which are invisible as they are concealed under the surface and which are rigidly connected to the tooth surfaces, are simultaneously moved along accordingly by calculation in the volume data record. A modified (simulated) volume data record thereby arises which can be output for representation purposes and which comprises the change in the tooth position ascertained by calculation. This simulated volume data record provides the treating physician with insight into the individual anatomical conditions of the patient; these can either be taken into account when planning an orthodontic repositioning measure or to visualize anatomical conditions following tooth repositioning without a new volume data record having to be created.

In a first application, the tooth movements performed during the therapy can hence be visualized using the procedure according to the present invention, also in view of the jaw anatomy within the scope of a follow-up. This follow-up can be performed multiple times during the treatment by the treating orthodontist in order to correct the treatment where necessary. Each checkup only requires the creation of a surface scan, which can be carried out in the orthodontic practice. The respective surface scan then serves as a basis for the creation, by calculation, of a corresponding simulated volume data record.

In a second application, tooth repositioning of the procedure according to the present invention can already be planned in advance taking into account the concealed jaw anatomy. The treating physician thereby creates a model of the subsequent tooth position with the aid of an orthodontic setup and creates a surface scan of the model. In this application, the surface scan of the model serves as a basis for the creation, by calculation, of the corresponding simulated volume data record, from which the treating physician can identify the anatomical effects the planned tooth repositioning would have.

The present invention is described below using a plurality of exemplary embodiments on the basis of the drawings.

Figure 1:
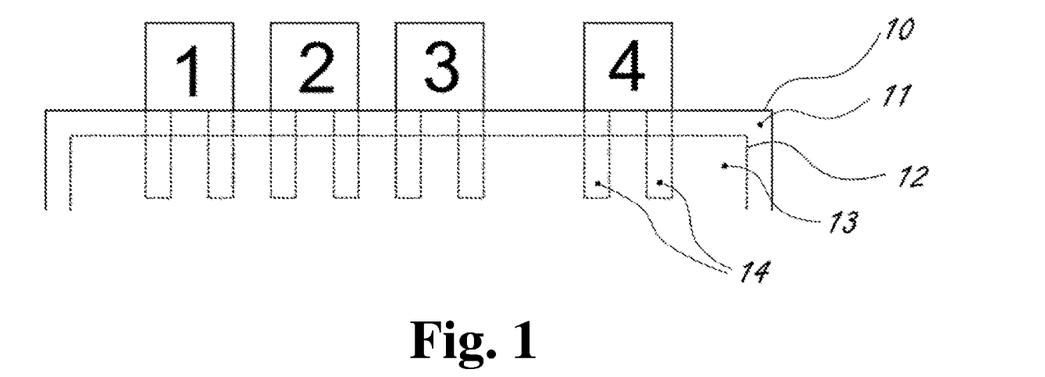
FIG. 1 shows a schematic anatomical situation in the jaw of a patient.

FIG. 1 initially shows the sketch of an anatomical initial situation in the jaw of a patient in which four teeth 1, 2, 3 and 4 are disposed with partly different spacings. Illustrated, firstly, is the surface 10 of the jaw mucosa 11, which forms a boundary to the air. On the other side, the jaw mucosa 11 forms a boundary 12 to the jaw bone 13, in which the roots 14 are seated.

Figure 2:
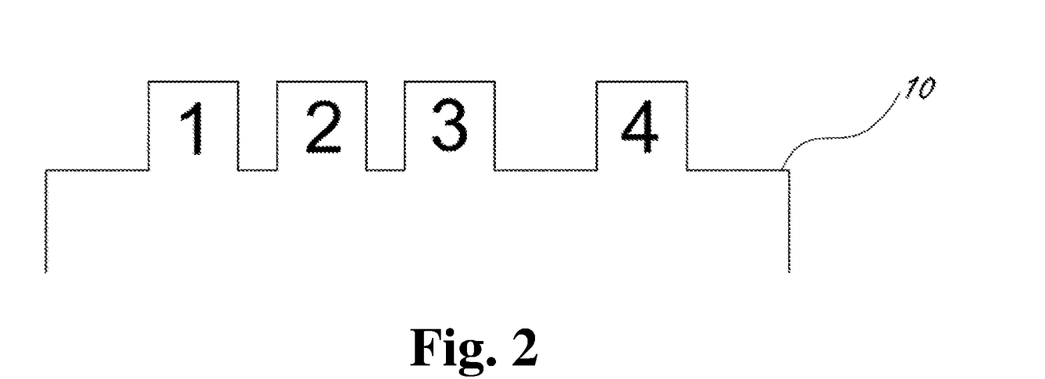
FIG. 2 shows the schematic result of an optical surface scan of the anatomical situation.

FIG. 2 illustrates the result of an optical surface scan of the jaw from FIG. 1. FIG. 1 shows that the surface scan only captures the visible surfaces of the teeth 1 to 4 and the surface 10 of the jaw mucosa 11.

Figure 3:
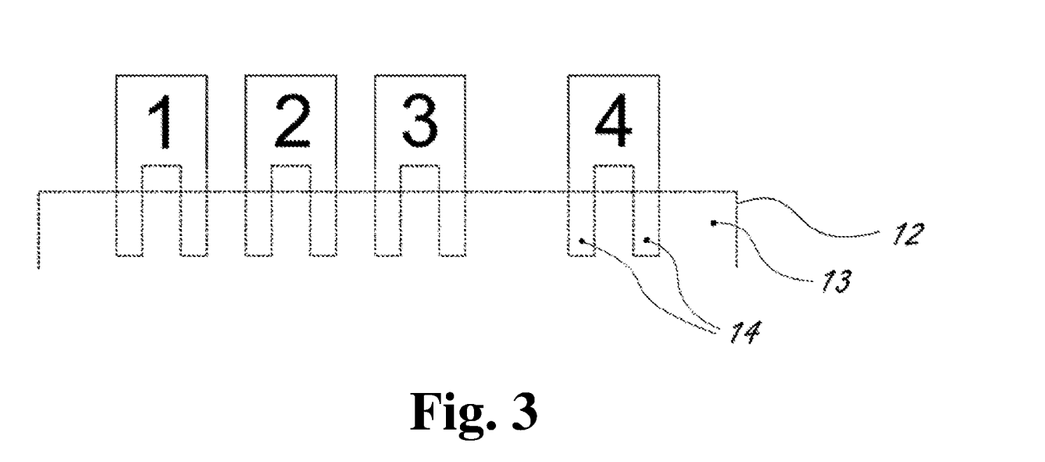
FIG. 3 shows the schematic result of a DVT recording of the anatomical situation.

In contrast thereto, FIG. 3 shows the result of a DVT recording, recorded by a digital volume tomography device, for example, a cone beam CT device. Although hard structures under the surface can be represented in such a three-dimensional data record, the boundaries of soft tissue can only be resolved with difficulty. In this respect, the hard teeth 1 to 4 with their roots 14, the jaw bone 13 and the boundary 12 between jaw bone 13 and jaw mucosa 11 can be identified in such a DVT recording.

The first exemplary embodiment to be described relates to the first application of the anatomical follow-up of orthodontic tooth repositioning, wherein the tooth repositioning is implemented using a removable orthodontic apparatus, for example, in this case conventional braces. The exemplary embodiment is described on the basis of FIG. 4. This exemplary embodiment is particularly relevant to cases where only soft tissue can serve as a reference structure since all teeth have moved. A second optical surface data record is required since the reference structures are not visible in the DVT data.

Figure 4:
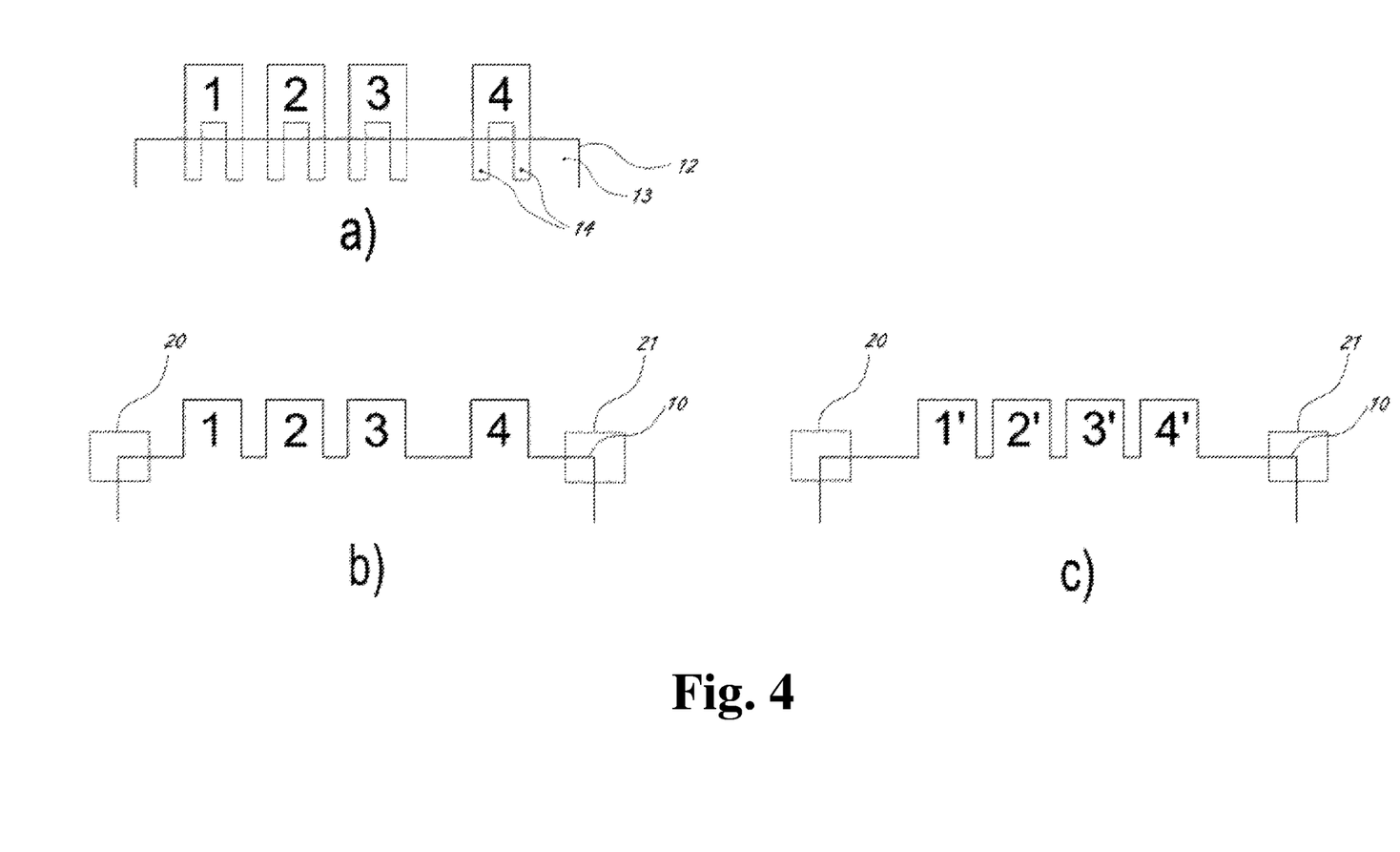
FIG. 4 shows a sketch of the embodiment with two surface scans.

A DVT recording of the patient and a set of surface data of the patient or of the model are created at the start of the therapy at a time T0 for this first exemplary embodiment. It is evident from a) of FIG. 4 that the teeth 1 to 4 assume their original position. The roots 14 and the boundary 12 of the jaw bone 13 can be identified in the DVT recording. In comparison, b) of FIG. 4 shows the same situation at the time T0 as recorded by an optical scanner. By contrast, c) of FIG. 4 represents the situation following a therapeutic displacement of the teeth 1 to 4 at a time T1. Unlike the teeth 1 to 4, the regions 20 and 21 of the jaw mucosa, identifiable in the surface data, have not changed and can therefore be used as a fixed reference structure.

This exemplary embodiment is accordingly accompanied by the following steps, which need not necessarily be worked through in the sequence as listed:

1. Prior to the treatment (at the time T0) firstly, a DVT data record DVT_T0 and, secondly, a first optical surface data record OO_T0 of a patient are recorded, in particular within the scope of a tooth status check.
2. Once the treatment has advanced to time T1, the occlusal status of the patient is scanned using an intraoral camera, and hence the further surface data record OO_T1 is recorded, with this recording being implemented without an orthodontic apparatus in the mouth of the patient.
3. Subsequently, the registration between the data records DVT_T0 and OO_T0 is performed. Since both of the data records are an image representation of the same unchanged tooth status at the time T0, they can be registered based on the crowns.
4. This is followed by the registration between the data records OO_T0 and OO_T1, within the scope of which regions along the tooth arch that have not changed are identified. The OO_T0 data is aligned with the OO_T1 data, or vice versa, on the basis of these fixed reference structures.
5. In the next step, only individual regions or parts in the OO_T0 data record are considered and aligned with the OO_T1 data via a "partly rigid" registration. A segmentation of the OO_T0 data record can be resorted to in this process. The segmentation defines the parts of the surface data OO_T0 that can be considered to be independent objects, and these can now be aligned with the OO_T1 surface data in an individual fashion ("partly rigid"). The segmentation may thus disclose each individual tooth as an independent object.
6. As a result of the partly rigid registration carried out in step 5), how a tooth has been moved between times T0 and T1 within the scope of the therapy is known for each (segmented) tooth or for each crown in the OO_T0 data.
7. The identified movements of the teeth (crowns) are then transferred to the DVT_T0 data. This is possible since the spatial relationships are known as a result of the registration between DVT_T0 and OO_T0. For example, if a certain tooth has been moved according to the transformation Transf_T0_T1 between times T0 and T1, this transformation is now transferred to the bony tissue in the DVT_T0 data below the crown and visualized. By extending the crown downward, it is possible to ascertain the corresponding root tissue of the tooth. The root tissue can alternatively be ascertained by segmenting the DVT_T0 data.
8. The teeth bite differently onto one another in centric occlusion in the new tooth position in OO_T1. The new centric occlusion position is transferred to the jaw joints to make visible where the jaw condyles are situated in relation to the jaw sockets. There is no need to create new DVT recordings for making visible the new situation which sets in as a result of the therapy.

Figure 5:
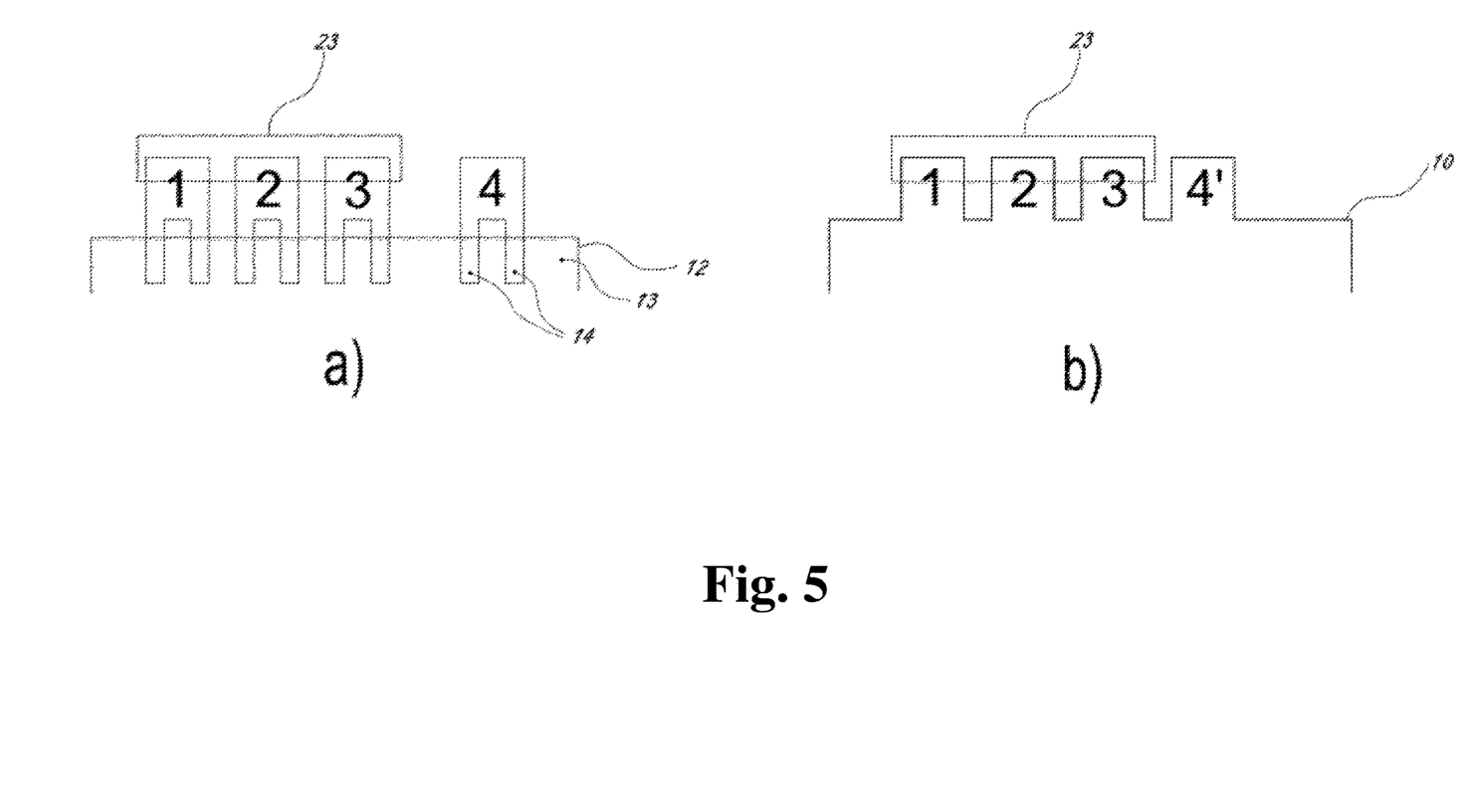
FIG. 5 shows a sketch of the embodiment with one surface scan.

The exemplary embodiment described below on the basis of FIG. 5 is similar to the first exemplary embodiment and accordingly relates to the first application. The difference lies in the fact that recording the first optical surface data record OO_T0 is dispensed with because a fixed reference structure, in particular unmoved teeth, can be chosen in this case, the fixed reference structure being visible both in the surface data and in the DVT data. Unmoved teeth are particularly suitable as a fixed reference structure as these cannot deform and have more geometric details that allow a more reliable spatial assignment.

A DVT data record at the time T0 is shown in a) of FIG. 5, and an optical surface data record at the time T1 is shown in b) of FIG. 5. The comparison of the data records shows that only tooth 4 was moved into a position 4'. The region 23, in which the unmoved teeth 1 to 3 visible in the surface data record are situated, can be used as a fixed reference structure in this case.

1. Only a DVT data record DVT_T0 of a patient is recorded at the time T0 prior to the treatment, for example, within the scope of a tooth status checkup.
2. Once the treatment has advanced to the time T1, the occlusal status of the patient is scanned using an intraoral camera and a surface data record OO_T1 is recorded, this recording once again being made without the orthodontic apparatus in the mouth of the patient.
3. Subsequently, the surface data OO_T1 is registered with the DVT data DVT_T0 on the basis of the fixed reference structure 23. Teeth or jaw regions that have not moved since T0 are thereby marked in the surface data record OO_T1. This can be implemented by hand or by an algorithm. The OO_T1 data is then registered in rigid fashion to the DVT_T0 data, with only teeth or jaw regions marked previously being used for the registration.
4. Registering the occlusal status at the time T1 is then carried out with the DVT data record DVT_T0 on the basis of a partly rigid registration, with the crowns visible in the surface data record OO_T1 being merged with the DVT data DVT_T0 and the tooth movements being transferred to the DVT data in the process. The regions that have moved since the time T0, i.e., the non-marked regions, are here considered in the OO_T1 data. These are then registered with the DVT_T0 data in a partly rigid fashion, in particular with the aid of a segmentation.
5. Within the scope of the partly rigid registration carried out in step 4), the transformation vector with which a tooth has moved between T0 and T1 is known from the OO_T1 data for each (segmented) tooth.
6. The identified transformation vectors of the teeth (crowns) are then transferred to the DVT_T0 data. For example, if a certain tooth has been moved according to the transformation Transf_T0_T1 between times T0 and T1, this transformation is now also transferred within the DVT_T0 data to the bony tissue below the crown, that is invisible in the surface data, and visualized. By "extending" the crown downward in such a way, it is possible to ascertain the corresponding root tissue of the tooth. The root tissue can alternatively be ascertained by segmenting the DVT_T0 data.
7. The teeth bite differently onto one another in centric occlusion in the new position in OO_T1. The new centric occlusion position is transferred to the jaw joints to make visable where the jaw joints are situated. There is no need to create new DVT recordings for making visible the new situation which sets in as a result of the therapy.

In accordance with the following third exemplary embodiment, which also relates to the first application, an anatomical follow-up of a therapy can be carried out with a secured orthodontic apparatus. The sequence of steps here corresponds to that of the first exemplary embodiment, wherein the dental braces, which are securely seated on the teeth and hence visible in the OO_T1 data, are masked before the OO_T1 data is registered with the OO_T0 data. The same can also happen in accordance with the steps of the aforementioned modified first exemplary embodiment, wherein the dental braces, which are securely seated on the teeth and hence visible in the OO_T1 data, are masked before the data is registered with the DVT_T0 data.

The third exemplary embodiment, described below, relates to the second application and accordingly facilitates the visualization of the anatomical effects on the basis of a conventional orthodontic setup. The subsequent sequence of steps is once again not mandatory, at least in respect of some of the steps:

1. A three-dimensional DVT data record DVT_T0 of the patient is initially created at the time T0 prior to the orthodontic treatment.
2. A conventional orthodontic setup is carried out on the basis of a cast plaster model. The surface of the plaster model is thereby initially scanned using an optical scanner and the surface data record OO_T0 is thus created.
3. The plaster model is subsequently sawed up so that the teeth that are decisive for the therapy can be detached and separately brought into the orthodontic target position. The teeth are in particular affixed with a (red) dyed wax in the planned target position.
4. The now existing modified plaster model, which represents the tooth position that should be achieved by the therapy, is scanned using an optical scanner to create the surface data record OO_T1. Should the scanner identify colors, the altered region, which accordingly cannot be found in the original 00_T0 data record, can be identified on the basis of the (red) color of the wax.
5. The original surface data record OO_T0 is registered with the DVT data DVT_T0.
6. The surface data record OO_T0 is also registered with the surface data record OO_T1. Regions, in particular gingiva regions, which have not altered during the therapy are thereby initially identified. The (red) dyed wax regions, in which the tooth position has been altered in the model, are not taken into account, neither are teeth are that have been separated from the gingiva by (red) wax.
7. The regions that were altered in the model are subsequently registered in a partly rigid fashion from the surface data record OO_T0 to the surface data record OO_T1. A segmentation can here once again be resorted to.
8. The movements of the crowns thus ascertained are transferred onto the roots and onto the jaw joints in the DVT data record as described in the above exemplary embodiments. A simulated volume data record of the tooth repositioning that was planned using the plaster model thereby arises. The treating physician can identify the consequences of the planned therapy on the anatomy of the patient based on this simulated volume data record.

The next exemplary embodiment also relates to the second application of therapy planning. No surface data record OO_T0 of the unaltered plaster impression is available in this case.
1. A DVT data record DVT_T0 of the patient is available at the time T0 in advance of the orthodontic treatment.
2. A conventional orthodontic setup is carried out on the basis of a plaster model.
3. The plaster model is sawed up so that the teeth that are decisive for the therapy can be detached and separately brought into the orthodontic target position. The teeth are in particular affixed with a (red) dyed wax in the planned target position.
4. The now existing modified plaster model, which represents the tooth position that should be achieved by the therapy, is scanned using an optical scanner to create the surface data record OO_T1. Should the scanner identify colors, the altered regions can be identified on the basis of the (red) color of the wax.
5. The surface data record OO_T1 thus created is registered with the DVT data DVT_T0. The teeth or jaw regions that have not been altered are identified therefor.
6. The regions that were altered within the scope of planning are then registered in a partly rigid fashion from 00_T1 on DVT_T0. A segmentation can be resorted to in the process.
7. The ascertained movements of the crowns are transferred to the roots in the DVT data and to the jaw joints. The simulated DVT volume data record, which should be associated with the plaster model of the planned teeth repositioning, serves to allow the treating physician to estimate the consequences of the planned therapy on the anatomy of the patient.

Three-dimensionally printed models can also be used instead of the plaster models. The process is as follows:
1. Tooth arches of the patient are initially recorded using an optical scanner. Artificial elevations are additionally provided in the scanning data level with the gingiva, the artificial elevations serving for subsequent registration.
2. The surface data record OO_T0, which is slightly modified in relation to the original, consequently arises.
3. The surface data record OO_T0 is printed using a 3D printer.
4. The print that has arisen on the basis of OO_T0 is then sawed apart and planning in the form of a setup is created. This step is the same as the one also carried out on the plaster model.
5. The now existing modified print, which represents the tooth position intended to be obtained by the therapy, is scanned using an optical scanner and the surface data record OO_T1 is created.
6. The created surface data record OO_T1 is registered with the DVT data DVT_T0. An improved registration between the surface data records OO_T0 and OO_T1 is possible as a result of the artificial and uniquely formed elevations introduced in step 1. The natural gingiva sometimes has too few details that can be used by a surface-based registration. The artificial elevations in contrast allow for a more reliable absolute spatial assignment.

Instead of using an optical scan of a three-dimensionally printed model or of a plaster model for producing the surface data record as in the exemplary embodiments described above, it is also possible to produce the surface data record of the altered tooth position by calculation from an available surface data record of the original, not yet altered, tooth position on a computer by way of a simulation ("digital setup"). A digital setup is used directly for visualizing the anatomical effects in this case.

According to the exemplary embodiment described above, this works even if no surface data is available prior to the treatment at the time T0.

Instead of the "positive" plaster model of the (planned) tooth position, it is also possible to use the "negative" impression itself or in the form of an orthodontic aligner. The visualization of the anatomical effects can accordingly be implemented in the style of a follow-up on the basis of such an aligner or an aligner set. If the aligner has not yet been worn by the patient, for example, because it is part of a series of aligners and should only be worn in a couple of months, the method offers a view into the future as to how the roots will be oriented after the use of the aligner. The method can, for example, be performed as follows:
1. A surface data record of the "negative" surface, which rests against the teeth when wearing the aligner, is first scanned using an intraoral camera or a laboratory scanner. This "negative" surface resting against the teeth can alternatively also be produced from the digital geometry data of a virtually planned aligner.
2. The surface data record of the tooth inner surfaces is registered on the crowns in the DVT data record using the registration method.
3. It is thereby possible to visualize the anatomical effects of the aligner without having to create a new DVT. The same can also be implemented for a series of aligners. It is thereby possible to visualize the effects of the aligner series on roots and jaw joints. This serves to forensically secure an orthodontic treatment even in relation to the jaw joints. There can here also be an animation in the 3D DVT data and in views calculated from the DVT data, such as a panoramic view or calculated cephalometric views, the animation showing the anatomical sequence from the initial situation to the target situation.

A reference body is used in a further exemplary embodiment, with which the assignment between the CAD/CAM data and the DVT data can be ascertained during the progress of the treatment. The use of such a reference body is helpful if no OO_T0 data is available. The reference body is placed into the mouth and also scanned at the time OO_T1. The reference body is thereby provided to always be in a fixed or known relationship with the jaw anatomy which does not move during tooth movements.

If the reference body is fastened to a tooth that has in the meantime been moved, the reference body must be altered during the second scan so that the hot spot of the reference body is at the same absolute position in relation to the jaw as in the first scan. This can be provided if the absolute movement of this tooth is known.

This procedure is a quasi "counterpart" to the application example set forth above of the visualization of the anatomical effects of conventional orthodontic setups on the basis of printed models, with a referencing aid being attached not to the printed setup but to the patient in this case. The concept lies in the reference body being attached to a tooth at the time T_O and also being scanned at least in the surface data. The reference body advantageously has parts that are easily identifiable both in the surface data and in the DVT data.

The present invention is not limited to embodiments described herein; reference should be had to the appended claims.

What is claimed is:

1. A method for representing a change in a tooth position in a jaw, the method comprising:
   creating a volume data record of an initial position of a plurality of teeth in a maxilla or in a mandible;
   ascertaining teeth boundaries from the volume data record;
   creating a surface data record following a real change or a virtual change in the tooth position, the surface data record comprising at least one of surface data of the teeth and at least parts of the volume data record comprising the jaw in an altered tooth position;
   referencing the surface data record with the volume data record via a reference structure existing in the surface data record, the reference structure not being affected by the change in the tooth position;
   after the referencing of the surface data record, transforming the change in the tooth position in the volume data record via a first calculation to align the teeth boundaries ascertained from the volume data record with the surface data of corresponding teeth from the surface data record so that tooth structures contained in the volume data record and concealed under a surface are moved via the first calculation; and
   outputting an altered volume record for representation purposes, the altered volume record comprising the change in the tooth position ascertained by the first calculation.

2. The method as recited in claim 1, wherein the surface data record is created using an optical scanning method either following the real change in the tooth position or following a change in the tooth position in a model.

3. The method as recited in claim 1, wherein the surface data record is created by the virtual change in the tooth position in an original surface data record.

4. The method as recited in claim 3, further comprising:
   recording the original surface data record at a first time;
   performing a registration between the original surface data record and the volume data record;
   ascertaining an unaltered reference structure based on the original surface data record and the surface data record; and
   performing a registration between the original surface data record and the surface data record via the reference structure;
   wherein,
   the transforming in the volume data record is implemented based on ascertained movements of crowns.

5. The method as recited in claim 1, wherein,
   the reference structure is extracted from the volume data record by a second calculation based on tissue boundaries comprising at least one of teeth and jaw portions, and
   the referencing of the volume data record with the surface data record is based on the reference structure.

6. The method as recited in claim 1, wherein,
   the surface data record is created from a model of the plurality of teeth by an optical scanning method, and
   the model is produced by an impression of the altered tooth position, or
   the model is produced by an impression of an original tooth position, and
   at least one of the plurality of teeth is removed from the model produced and reattached in an altered position.

7. The method as recited in claim 1, wherein,
   the surface data record is created from a model of the plurality of teeth by an optical scanning method, and
   the model is created by a 3D printer.

8. The method as recited in claim 1, wherein the surface data record is created by scanning the surfaces of an individually manufactured correcting splint which is applied to at least one of the plurality of teeth.

9. The method as recited in claim 8, wherein the individually manufactured correcting splint is an aligner.

10. The method as recited in claim 8, further comprising:
    performing a surface scan on a patient with a reference body attached to at least one of at least one of the plurality of teeth and the jaw.

11. A system for implementing the method as recited in claim 1.

12. A method for representing a change in a tooth position in a jaw, the method comprising:
    creating a volume data record of an initial position of a plurality of teeth in a maxilla or in a mandible;
    ascertaining teeth boundaries from the volume data record;
    creating a surface data record following a real change in the tooth position, the surface data record comprising at least one of surface data of the teeth and at least parts of the volume data record comprising the jaw in an altered tooth position;
    referencing the surface data record with the volume data record via a reference structure existing in the surface data record, the reference structure not being affected by the change in the tooth position;
    after the referencing of the surface data record, transforming the change in the tooth position in the volume data record via a first calculation to align the teeth boundaries ascertained from the volume data record with the surface data of corresponding teeth from the surface data record so that tooth structures contained in the volume data record and concealed under a surface are moved via the first calculation; and outputting an altered volume record for representation purposes, the altered volume record comprising the change in the tooth position ascertained by the first calculation.

\* \* \* \* \*